(12) United States Patent
Tan et al.

(10) Patent No.: US 10,682,602 B2
(45) Date of Patent: Jun. 16, 2020

(54) NANOFIBROUS FILTER

(71) Applicant: National University of Singapore, Singapore (SG)

(72) Inventors: Swee Ching Tan, Singapore (SG); Varun Kumar Singh, Singapore (SG); Sai Kishore Ravi, Singapore (SG)

(73) Assignee: National University of Singapore, Singapore (SG)

( * ) Notice: Subject to any disclaimer, the term of this patent is extended or adjusted under 35 U.S.C. 154(b) by 372 days.

(21) Appl. No.: 15/876,000

(22) Filed: Jan. 19, 2018

(65) Prior Publication Data
US 2019/0022570 A1    Jan. 24, 2019

(30) Foreign Application Priority Data
Jan. 19, 2017 (SG) .................. 0201700455T

(51) Int. Cl.
| | | |
|---|---|---|
| B01D 53/22 | (2006.01) | |
| B01D 46/54 | (2006.01) | |
| B01D 39/16 | (2006.01) | |
| C07D 487/22 | (2006.01) | |
| C07D 487/04 | (2006.01) | |
| B82Y 30/00 | (2011.01) | |
| B82Y 40/00 | (2011.01) | |

(52) U.S. Cl.
CPC ....... B01D 46/546 (2013.01); B01D 39/1623 (2013.01); C07D 487/04 (2013.01); C07D 487/22 (2013.01); B01D 2239/025 (2013.01); B01D 2239/0492 (2013.01); B01D 2239/0645 (2013.01); B01D 2239/10 (2013.01); B01D 2239/1233 (2013.01); B82Y 30/00 (2013.01); B82Y 40/00 (2013.01)

(58) Field of Classification Search
CPC .... C07D 487/22; C07D 487/04; B82Y 40/00; B82Y 30/00; B01D 2239/10; B01D 46/546; B01D 2239/1233; B01D 39/1623; B01D 2239/0492; B01D 2239/0645; B01D 2239/025
See application file for complete search history.

(56) References Cited

U.S. PATENT DOCUMENTS

| | | | | |
|---|---|---|---|---|
| 6,251,581 | B1* | 6/2001 | Ullman | G01N 33/586 435/4 |
| 2004/0126717 | A1* | 7/2004 | Nakagawa | G03C 1/346 430/523 |
| 2004/0234911 | A1* | 11/2004 | Suzuki | G03C 1/49872 430/619 |
| 2005/0004260 | A1* | 1/2005 | Taguchi | C09D 11/037 523/160 |
| 2005/0204952 | A1* | 9/2005 | Wachi | C09D 11/32 106/31.14 |
| 2007/0167537 | A1* | 7/2007 | Taguchi | C09D 11/328 523/160 |

(Continued)

Primary Examiner — Anthony R Shumate

(57) ABSTRACT

There is provided a nanofibrous filter comprising a substrate and self-assembled nanofibers deposited on the substrate. The self-assembled nanofibers comprise π-conjugated molecules self-assembled by non-covalent interactions, wherein the π-conjugated molecules are phthalocyanine derivative molecules or diketopyrrolopyrrole derivative molecules. There is also provided a method of preparing the nanofibrous filter.

17 Claims, 8 Drawing Sheets

(56) References Cited

U.S. PATENT DOCUMENTS

| | | | |
|---|---|---|---|
| 2009/0226835 A1* | 9/2009 | Mayo | B82Y 30/00 430/108.21 |
| 2010/0009214 A1* | 1/2010 | Sato | C09B 57/004 428/704 |
| 2011/0183123 A1* | 7/2011 | Buck | B81C 1/00206 428/195.1 |
| 2014/0072871 A1* | 3/2014 | Chen | H01M 4/36 429/213 |
| 2018/0250405 A1* | 9/2018 | Biel | A61K 47/6849 |
| 2019/0015510 A1* | 1/2019 | Makings | A61K 41/0076 |
| 2019/0365897 A1* | 12/2019 | Garcia-Guzman | A61P 35/00 |

* cited by examiner

NANOFIBROUS FILTER

TECHNICAL FIELD

The present invention relates to a nanofibrous filter and a method of making the same.

BACKGROUND

Particulate matter pollution in air poses a serious health threat and is responsible for thousands of deaths annually. Among particular matter particles, PM 2.5 mainly causes more morbidity and mortality worldwide after prolonged exposures, owing to their small particle size which can penetrate human bronchi and lungs compared to other larger size particulate matter resulting in lung disease, emphysema and lung cancer, especially in susceptible individuals and those suffering from respiratory and heart disease as their condition may be worsened by these particulate matter.

There are several filtration devices and systems currently in use. For example, modern commercial buildings have protection through filtering in ventilation systems which run on electricity and are often too noisy and even produce poisonous ozone gas. Individual safety masks like commercial respirators are commonly used as outdoor protection, which though prevent particle entry, make breathing difficult. Other common devices include air cleaning devices such as electrostatic precipitators and media filters which can be fitted to regulate particulate levels in buildings with central air conditioning systems. However, these devices are expensive and often not affordable to most housing societies. The existing air filter technology also has several shortcomings as most air purifiers are noisy and require filters to be replaced frequently. Further, ionizing air purifiers generate hazardous by-products like ozone gas which potentially causes respiratory ailments.

Recently, there has been a focus on developing nanofibrous materials for air filtration. A fibrous filter is comprised of a large number of randomly oriented fibers which form a dense material or mat which captures and retains particles throughout the depth or thickness. It is the thickness, fiber diameter, and density of the mat that enable fibrous filters to function. One such fibrous filter known in the art comprises advanced nanostructured carbon nanotube (CNT) structures, such as CNT/quartz-fiber nanotubes (CNTs). However, these are toxic. In another approach, several polymeric nanofibers, such as polyvinyl alcohol and poly-acrylonitrile with or without incorporation of nanoparticles, have been used and have shown good filtration efficiencies. However, the instability of nanoparticles over nanofibers is a concern. The nanofibers employed for air filters have been made by electrospinning, a process that utilizes an electric field applied to a drop of polymer melt or solution on the tip of the nozzle such that the droplet deforms and a charged jet accelerates toward the target, thereby generating nanofibers. However, the drawbacks of this technique are that it requires specialized equipment, high voltages, and electrically conductive targets and also suffers from a low deposition rate. Further, the diameters of electrospun fibers are much larger than the mean free path of air molecules and the mechanical properties of the electrospun fibers are not strong enough to be used in air filtration.

There is therefore a need for an improved nanofibrous filter for use in air filtration.

SUMMARY OF THE INVENTION

The present invention seeks to address these problems, and/or to provide an improved nanofibrous filter for use in air filtration.

In general terms, the invention relates to a nanofibrous air filter which is able to effectively capture harmful PM 2.5 particles and PM 10 particles. The nanofibrous air filter of the present invention has a good filtration efficiency while maintaining a low pressure drop across the filter. Accordingly, the nanofibrous air filter is suitable for use as a personal face mask, among other uses.

According to a first aspect, the present invention provides a nanofibrous filter comprising a substrate and self-assembled nanofibers deposited on the substrate, the self-assembled nanofibers comprising π-conjugated molecules self-assembled by non-covalent interactions, wherein the π-conjugated molecules are phthalocyanine derivative molecules or diketopyrrolopyrrole derivative molecules.

In particular, the nanofibrous filter may have a filtration efficiency of ≥80% for PM 2.5 particles and 85% for PM 10 particles. According to another particular aspect, the pressure drop across the filter may be ≤400 Pa.

The non-covalent interactions may be any suitable non-covalent interactions. For example, the non-covalent interactions may be any suitable intermolecular forces that occur between the different π-conjugated molecules. In particular, the non-covalent interactions may comprise π-π stacking, intermolecular hydrogen bonding, or a combination thereof.

The phthalocyanine derivative molecule may be any suitable phthalocyanine derivative molecule. According to a particular aspect, the phthalocyanine derivative molecule may be Compound I:

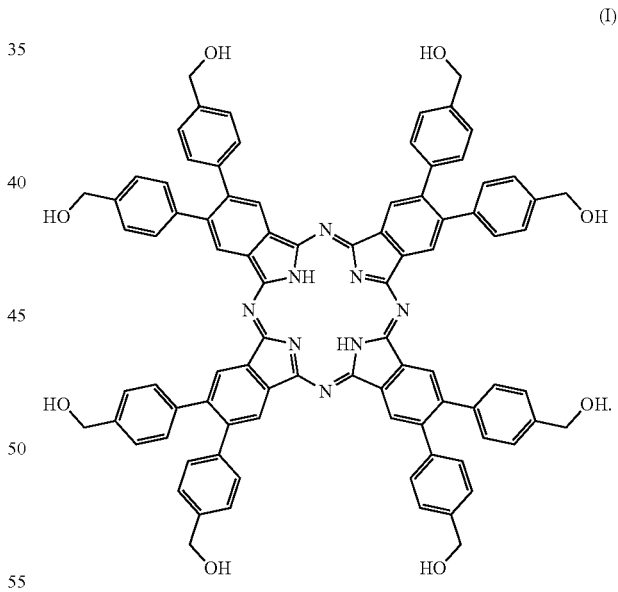

The Compound I may be formed by any suitable method. In particular, Compound I may be formed by cyclotetramerization of 4,4''-bis(hydroxymethyl)-[1,1':2',1''-terphenyl]-4',5'-dicarbonitrile in 1-pentanol.

The diketopyrrolopyrrole derivative molecule may be any suitable diketopyrrolopyrrole derivative molecule. According to another particular aspect, the diketopyrrolopyrrole derivative molecule may be Compound II:

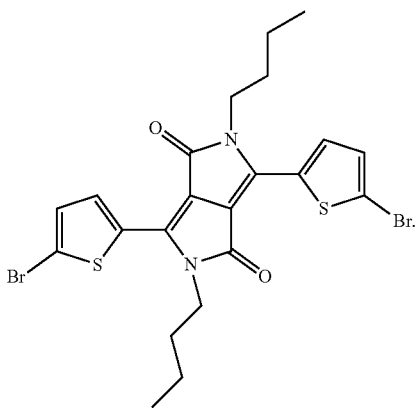

(II)

The nanofibers comprised in the nanofibrous filter may have a suitable average diameter. In particular, the average diameter of a nanofiber comprised within the nanofibrous filter may be 100-300 nm.

According to a second aspect, the present invention provides a method of preparing the nanofibrous filter described above. The method comprises:
- obtaining π-conjugated molecules, wherein the π-conjugated molecules are phthalocyanine derivative molecules or diketopyrrolopyrrole derivative molecules;
- dissolving the π-conjugated molecules in an organic solvent to form a solution comprising self-assembled nanofibers; and
- depositing the solution on a surface of a substrate to form the nanofibrous filter.

The π-conjugated molecules, including the phthalocyanine derivative molecules or diketopyrrolopyrrole derivative molecules may be as described above.

In particular, the obtaining may comprise synthesising the π-conjugated molecules. Even more in particular, when the π-conjugated molecule is a phthalocyanine derivative molecule, the obtaining may comprise synthesising the phthalocyanine derivative molecules by cyclotetramerization of 4,4"-bis(hydroxymethyl)-[1,1':2',1"-terphenyl]-4',5'-dicarbonitrile in 1-pentanol.

The organic solvent used in the dissolving may be any suitable organic solvent. For example, the organic solvent may be a polar solvent. In particular, the organic solvent may include, but is not limited to, dimethyl sulfoxide (DMSO), tetrahydrofuran (THF), dimethylformamide (DMF), dimethylacetamide (DMAc) or a combination thereof.

According to a particular aspect, when the π-conjugated molecule is phthalocyanine derivative molecule, the organic solvent used in the dissolving may be DMSO. According to another particular aspect, when the π-conjugated molecule is diketopyrrolopyrrole derivative molecule, the organic solvent used in the dissolving may be THF.

The dissolving may comprise dissolving a suitable concentration of π-conjugated molecules in the organic solvent. In particular, the dissolving may comprise dissolving the π-conjugated molecules to obtain a solution having a concentration of $10^{-4}$ M of the π-conjugated molecules when the π-conjugated molecule is phthalocyanine derivative molecule. In particular, the dissolving may comprise dissolving the π-conjugated molecules to obtain a solution having a concentration of $10^{-5}$ M of the π-conjugated molecules when the π-conjugated molecule is diketopyrrolopyrrole derivative molecule.

The depositing may comprise any suitable deposition method. For example, the deposition method may comprise drop-casting the solution on a surface of the substrate.

BRIEF DESCRIPTION OF THE DRAWINGS

In order that the invention may be fully understood and readily put into practical effect there shall now be described by way of non-limiting example only exemplary embodiments, the description being with reference to the accompanying illustrative drawings. In the drawings.

DETAILED DESCRIPTION

Figure 1:
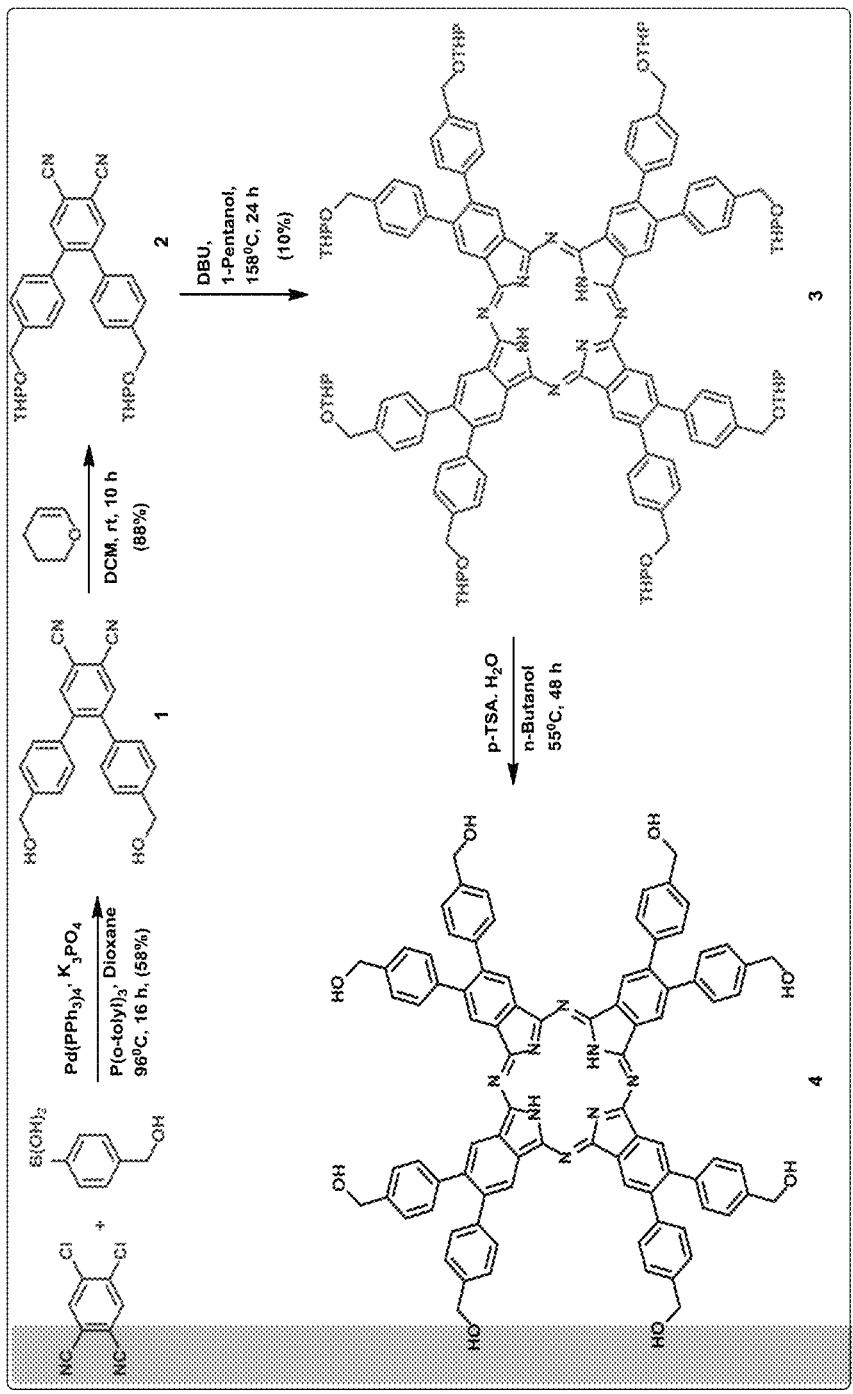
FIG. 1 shows a synthesis route for Compound I.

As explained above, there is a need for improved nanofibrous filter with a high filtration efficiency and reduced air flow resistance, as well as one with a low pressure drop.

The nanofibrous filter of the present invention captures the harmful PM particles, allows only fresh air to pass through and at the same time blocks harmful UV radiations. The fibrous filter is comprised of a large number of randomly oriented self-assembled nanofibers which form a dense material or mat which captures and retains particles throughout the depth or thickness. It is the thickness, fiber diameter, and density of the mat that enable fibrous filters to function.

The nanofibrous filter of the present invention relies on electrostatically charged nanofibers for capturing harmful PM 2.5 particles and PM 10 particles and may also simultaneously provide shielding from harmful ultraviolet (UV) radiation. Depending on the size of the particles, particulate matter is classified into two major groups. The bigger particles are called PM 10 which stands for particulate matter up to 10 μm in size and is composed mainly of smoke, dirt, and dust from factories. On the other hand, the smaller particles are called PM 2.5 and consist particles of up to 2.5 μm in size. PM 2.5 is composed of toxic organic compounds and heavy metals and is considered the most hazardous.

The nanofibers comprised in the nanofibrous filter are formed from self-assembly of specific organic molecules. The nanofibrous filter according to the present invention may be used in several applications such as personal face masks and as a window-based air filter system as a stand-alone device for achieving healthier indoor living environment. The nanofibrous filter according to the present invention does not require any electricity to run and also does not produce any hazardous by-products.

In particular, the nanofibrous filter comprises nanofibers which are formed from self-assembly of proper designing of the structure of the organic molecules. The nanofibrous filter is prepared without using electrospinning which may be expensive. In fact, the method of preparing the nanofibrous filter does not require any high voltage.

According to a first aspect, the present invention provides a nanofibrous filter comprising a substrate and self-assembled nanofibers deposited on the substrate, the self-assembled nanofibers comprising π-conjugated molecules self-assembled by non-covalent interactions, wherein the π-conjugated molecules are phthalocyanine derivative molecules or diketopyrrolopyrrole derivative molecules.

For the purposes of the present invention, self-assembled nanofibers are defined as nanofibers which are formed by self-assembly in which π-conjugated molecules are spontaneously organized into an aggregate with a well-defined structure to form the nanofibers. In particular, the π-conjugated molecules are self-assembled by weak non-covalent interactions.

The non-covalent interactions may be any suitable non-covalent interactions. For example, the non-covalent interactions may be any suitable intermolecular forces that occur between the different π-conjugated molecules. In particular, the non-covalent interactions may comprise π-π stacking, intermolecular hydrogen bonding, or a combination thereof.

The π-conjugated molecules may be functionalized to enable π-π stacking and intermolecular hydrogen bonding to form t-stack architecture with π-conjugated molecules on top of each other, thereby forming nanofibers. In particular, the π-conjugated molecules may be phthalocyanine derivative molecules or diketopyrrolopyrrole derivative molecules.

The phthalocyanine derivative molecule may be any suitable phthalocyanine derivative molecule. Phthalocyanine derivative molecules are macrocyclic planar molecules with good thermal and photochemical stability, as well as transparency over a large portion of the visible spectrum. According to a particular aspect, the phthalocyanine derivative molecule may be functionalised such that the peripheral positions comprise a hydroxyl group to enable π-π stacking and intermolecular hydrogen bonding to form π-stack architecture. In particular, the phthalocyanine derivative molecule may be Compound I:

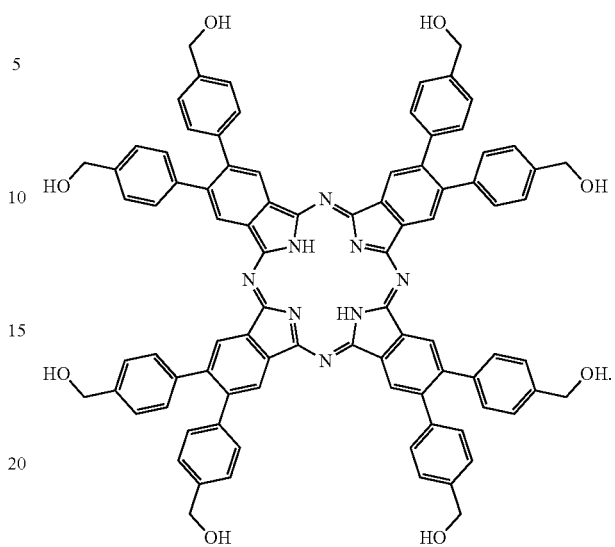

(I)

Figure 2A:
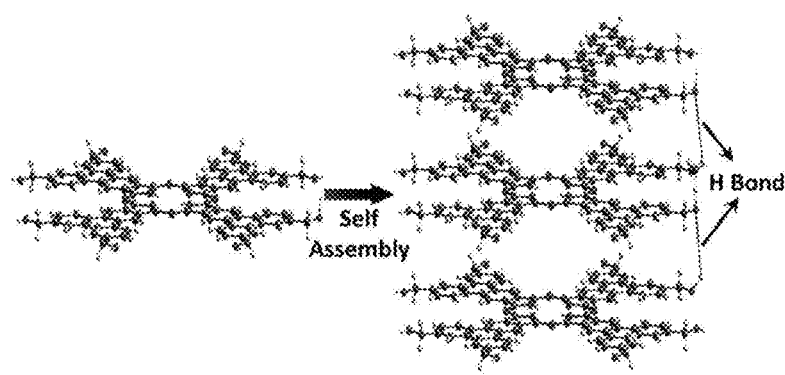
FIG. 2(a) shows a schematic representation of the molecules of Compound I and FIG. 2(b) shows a scanning electron microscope (SEM) micrograph of nanofibers of Compound I.
Figure 2B:
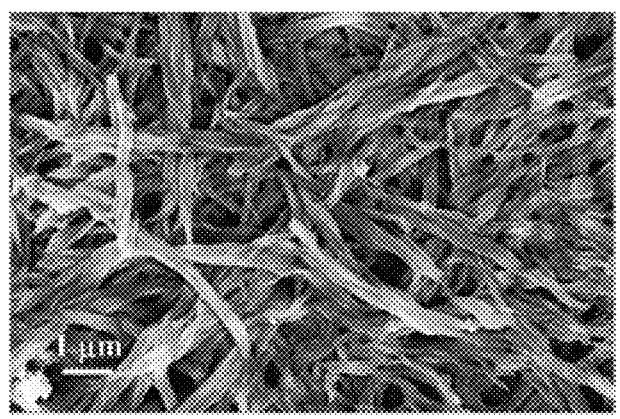

The Compound I may be formed by any suitable method. In particular, Compound I may be formed by cyclotetramerization of 4,4"-bis(hydroxymethyl)-[1,1':2',1"-terphenyl]-4', 5'-dicarbonitrile in 1-pentanol. FIG. 1 shows the synthesis of Compound I and FIG. 2(a) shows the π-π stacking and intermolecular hydrogen bonding network which leads to the formation of the nanofibers as shown in FIG. 2(b).

The diketopyrrolopyrrole derivative molecule may be any suitable diketopyrrolopyrrole derivative molecule. Diketopyrrolopyrrole derivative molecules are chromophores and have a planar structure. According to a particular aspect, the diketopyrrolopyrrole derivative molecule may have a tendency to form enable π-π stacking and intermolecular hydrogen bonding with neighbouring diketopyrrolopyrrole derivative molecules to form π-stack architecture. In particular, the diketopyrrolopyrrole derivative molecule may be Compound II:

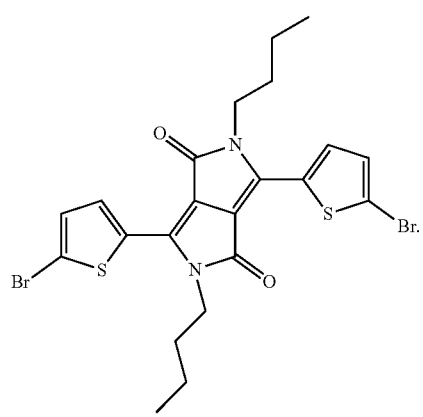

(II)

Figure 3:
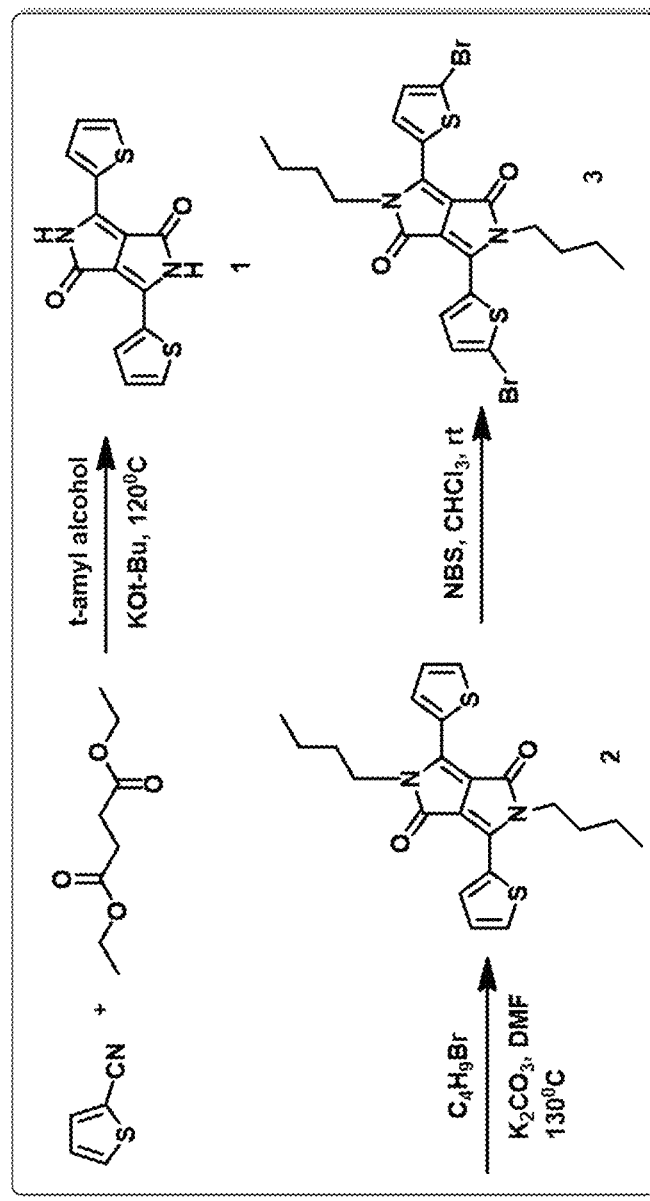
FIG. 3 shows a synthesis route for Compound II.
Figure 4:
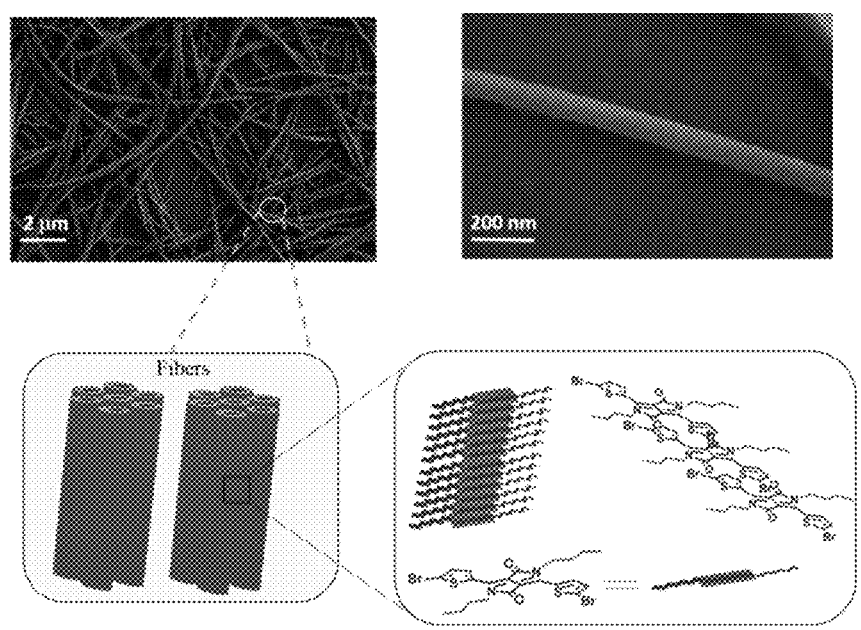
FIG. 4 shows the SEM images of the nanofibers of Compound II and a schematic representation of the molecules of Compound II.

The Compound II may be formed by any suitable method. FIG. 3 shows the synthesis of Compound II and FIG. 4 shows the π-π stacking and intermolecular hydrogen bonding network which leads to the formation of the nanofibers. For example, the self-assembly of the diketopyrrolopyrrole derivative molecules may be driven by J-type aggregation between the diketopyrrolopyrrole derivative molecules.

The nanofibers comprised in the nanofibrous filter may have a suitable average diameter. For example, the average diameter of a single nanofiber comprised within the nanofibrous filter may be 100-300 nm. In particular, the average diameter of a single nanofiber may be 100-300 nm, 120-280 nm, 150-250 nm, 180-220 nm, 200-210 nm. Even more in particular, the average diameter of a single nanofiber may be 150-250 nm. Accordingly, the nanofibers have a large specific area and good adsorption capacity.

Figure 5A:
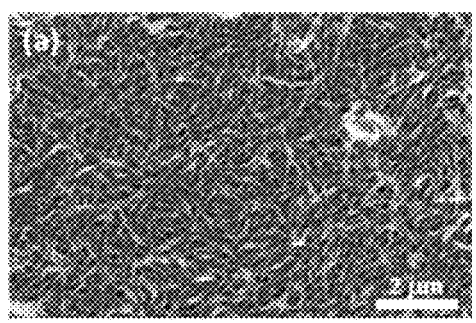
FIG. 5(a) shows a SEM image of a nanofibrous filter comprising nanofibers of Compound I before particulate matter deposition and FIG. 5(b) shows a SEM image of a nanofibrous filter comprising nanofibers of Compound I after particulate matter deposition.

The nanofibrous filter of the present invention has good filtration efficiency due to the closely spaced nanofibers comprised in the nanofibrous filter. The filtration efficiency is defined as a measure of how efficiently the nanofibrous filter is able to remove PM particles. The filtration efficiency may be obtained by comparing the PM particle number concentration with and without the use of the nanofibrous filter. For example, the nanofibrous filter may have a filtration efficiency of ≥80% for PM 2.5 particles and ≥85% for PM 10 particles. In particular, the filtration efficiency may be ≥85% for PM 2.5 particles and ≥90% for PM 10 particles. FIGS. 5(a) and (b) shows the scanning electron microscope (SEM) images of the nanofibrous filter comprising nanofibers from Compound I according to one embodiment of the present invention before and after, respectively, exposure to hazardous PM pollutants.

Another factor which determines the efficiency and potential of air filters is by accessing the results of a breathability test or measuring the pressure drop across the filter. The pressure drop may be caused by the combined effects of the resistance of each nanofiber comprised in the nanofibrous filter to the flow of air past it. Accordingly, the lower the pressure drop, the better the air filter. In particular, a highly efficient air filter should have a good balance between PM particle filtration efficiency and pressure drop. According to another particular aspect, the pressure drop across the filter may be 400 Pa. The pressure drop across the filter may be measured at a suitable face velocity such as 3 ms$^{-1}$. In particular, the pressure drop may be 374 Pa.

Further, the nanofibrous filter may have an optical transparency. Accordingly, the filter may be suitable for use as a standalone device on windows, such that the filter is able to filter any harmful particles from the air entering the window without affecting the amount of light coming through the window.

According to a second aspect, the present invention provides a method of preparing the nanofibrous filter described above. The method comprises:
    obtaining π-conjugated molecules, wherein the π-conjugated molecules are phthalocyanine derivative molecules or diketopyrrolopyrrole derivative molecules;
    dissolving the π-conjugated molecules in an organic solvent to form a solution comprising self-assembled nanofibers; and
    depositing the solution on a surface of a substrate to form the nanofibrous filter.

The π-conjugated molecules, including the phthalocyanine derivative molecules or diketopyrrolopyrrole derivative molecules may be as described above.

In particular, the obtaining may comprise synthesising the π-conjugated molecules. Even more in particular, when the π-conjugated molecule is a phthalocyanine derivative molecule, the obtaining may comprise synthesising the phthalocyanine derivative molecules by cyclotetramerization of 4,4"-bis(hydroxymethyl)-[1,1':2',1"-terphenyl]-4',5'-dicarbonitrile in 1-pentanol.

According to a particular aspect, the phthalocyanine derivative molecule may be Compound I and the obtaining may comprise synthesising Compound I according to the synthesis scheme as shown in FIG. 1.

According to another particular aspect, the diketopyrrolopyrrole derivative molecule may be Compound II and the obtaining may comprise synthesising Compound II according to the synthesis scheme as shown in FIG. 3.

The organic solvent used in the dissolving may be any suitable organic solvent. For example, the organic solvent may be a polar solvent. In particular, the organic solvent may include, but is not limited to, dimethyl sulfoxide (DMSO), tetrahydrofuran (THF), dimethylformamide (DMF), dimethylacetamide (DMAc) or a combination thereof.

According to a particular aspect, when the π-conjugated molecule is phthalocyanine derivative molecule, the organic solvent used in the dissolving may be DMSO. According to another particular aspect, when the π-conjugated molecule is diketopyrrolopyrrole derivative molecule, the organic solvent used in the dissolving may be THF.

The dissolving may comprise dissolving a suitable concentration of π-conjugated molecules in the organic solvent. In particular, the dissolving may comprise dissolving the π-conjugated molecules to obtain a solution having a suitable concentration so as to enable the formation of the nanofibers. Even more in particular, the dissolving may comprise dissolving the π-conjugated molecules to obtain a solution having a concentration of ≥10$^{-4}$ M of the π-conjugated molecule when the π-conjugated molecule is phthalocyanine derivative molecule. According to another particular aspect, the dissolving may comprise dissolving the π-conjugated molecules to obtain a solution having a concentration of ≥10$^{-5}$ M of the π-conjugated molecule when the π-conjugated molecule is diketopyrrolopyrrole derivative molecule.

The depositing may comprise any suitable deposition method. For example, the deposition method may comprise drop-casting the solution on a surface of the substrate.

Any suitable substrate may be used for the purposes of the present invention. For example, the substrate may be, but not limited to, a silicon substrate or a polyester cloth.

Whilst the foregoing description has described exemplary embodiments, it will be understood by those skilled in the technology concerned that many variations may be made without departing from the present invention.

Having now generally described the invention, the same will be more readily understood through reference to the following examples which are provided by way of illustration, and are not intended to be limiting.

EXAMPLE

Example 1

Materials 4,5-dichlorophthalonitrile, 4-(Hydroxymethyl)phenylboronic acid, potassium phosphate tribasic,o-tritolylphosphine, 1,4-dioxane,anhydrous, dichloromethane, Tetrakis (triphenylphosphne)palladium(0), 3,4-Dihydro-2H-pyran, 1,8 Diazabicyclo[5.4.0]undec-7-ene (DBU), 1-Pentanol, p-Toluenesulphonic acid dihydrate, n-butanol, anhydrous dimethyl sulfoxide, Deuterated chloroform were purchased from sigma Aldrich and were used as received.

Synthesis of Compound I

The synthesis of Compound I was using the scheme as shown in FIG. 1.

(i) Synthesis of 4,4''-bis(hydroxymethyl)-[1,1':2',1''-terphenyl]-4',5'-dicarbonitrile (1)

A double neck round bottom flask was charged with 4,5-dichlorophthalonitrile (0.8 g, 4.06 mmol), 4-hydroxymethylphenylboronic acid (2.35 g, 315.42 mmol), tri(o-tolyl) phosphine (0.25, 0.81 mmol), potassium phosphate tribasic (5.16 g, 24.36 mmol) and evacuated and refilled with nitrogen three times over a schlenck line, then $Pd(PPh_3)_4$ (0.093 g, 0.08 mmol) was added and again purged with nitrogen. Then 10 ml of anhydrous 1,4-dioxane was added and the mixture was heated at 94° C. for 15 h. After the reaction mixture was filtered over celite and concentrated on a rotary evaporator, it was then subjected to silica gel column chromatography using hexane:ethyl acetate as eluent; yellow powder (isolated yield 58%). Elemental analysis calculations for $C_{22}H_{16}N_2O_2\%$ (340.37): C, 77.63; H, 4.74; N, 8.23. Found: C, 77.59; H, 4.73; N, 8.57. $^1H$ NMR (300 MHz, DMSO-$d_6$) δ 8.17 (s, 2H), 7.25 (d, J=7.91 Hz, 4H), 7.14 (d, J=7.91 Hz, 4H), 4.48 (s, 4H). ESI-MS (m/z): 340 $[M]^+$.

(ii) Synthesis of 4,4''-bis(((tetrahydro-2H-pyran-2-yl)oxy)methyl)-[1,1':2',1''-terphenyl]-4',5'-dicarbonitrile (2)

A single neck round bottom flask was charged with 1 (0.4 g, 1.17 mmol), p-TSA.$H_2O$ (0.009 g, 0.05 mmol) and dissolved in DCM then dihydropyran was added dropswise and the reaction mixture was allowed to stir for 10 h. After it was washed with water and extracted with DCM, concentrated and purified by column chromatography using Hexane:Ethyl acetate as eluent; viscous yellow oil (isolated yield 88%). Elemental analysis calculations for $C_{32}H_{32}N_2O_4\%$ (508.61): C, 75.57; H, 6.34; N, 5.51. Found: C, 75.23; H, 6.35; N, 5.58. $^1H$ NMR (300 MHz, CDCl$_3$) δ 7.75 (s, 2H), 7.29 (d, J=8.29 Hz, 4H), 7.09 (d, J=8.29 Hz, 4H), 4.78 (d, 2H), 4.69 (t, 2H), 4.49 (d, 2H), 3.86-3.79 (m, 2H), 3.50-3.43 (m, 2H), 1.9-1.6 (m, 12H). ESI-MS (m/z): 508 $[M]^+$.

(iii) Synthesis of THP Protected Phthalocyanine (3)

In a single neck RB flask 2 (0.1 g, 0.197 mmol) was taken and dissolved in 3 mL of 1-pentanol and the mixture was heated to 100° C. and DBU (catalytic amount) was added. The reaction mixture was heated to 160° C. for 24 h. After the reaction completed, resultant mixture was precipitated with methanol and washed three-four times and then filtered over a Buchner funnel and then purified by silica gel column chromatography using DCM:Methanol as eluent; green powder (isolated yield 15%). Elemental analysis calculations for $C_{128}H_{130}N_8O_{16}\%$ (2036.45): C, 75.49; H, 6.43; N, 5.50. Found: C, 75.43; H, 6.44; N, 5.58. $^1H$ NMR (300 MHz, CDCl$_3$) δ 9.08 (br s, 8H), 7.72-7.69 (m, 32H), 4.91 (d, 8H), 4.83 (t, 8H), 4.61 (d, 8H), 4.06-3.96 (m, 8H), 3.68-3.59 (m, 8H), 1.67-1.51 (m, 48H). MALDI-TOF Calculated for $C_{128}H_{130}N_8O_{16}$ $[M]^+$: 2036.45. Found: 2036.22.

(iv) Synthesis of Deprotected Phthalocyanine (4) (Compound I)

Compound 3 (0.004 g, 0.019 mmol) was taken in a single neck RB flask and dissolved in 1-butanol (16 mL), then p-TSA.$H_2O$ (0.022 g, 0.115 mmol) was added and was continued to stir at 60° C. for 48 h. After butanol was evaporated and the resultant mixture was precipitated with methanol and filtered and washed several times with methanol and DCM, dried in a hot air vacuum oven; green powder (isolated yield 77%). $^1H$ NMR (300 MHz, DMSO-$d_6$) δ 8.44 (br s, 8H), 7.38-7.27 (m, 32H), 5.38-5.29 (m, 8H), 4.66-4.56 (m, 16H), NH protons not observed. MALDI-TOF Calculated for $C_{88}H_{66}N_8O_8$ $[M]^+$: 1362.50. Found: 1363.69.

Self-Assembly of Nanofibers

When Compound I was dissolved in dimethyl sulfoxide (DMSO) at a concentration of 2.0 mg/mL, a visually transparent green solution was obtained. After standing in a sealed vial at ambient temperature overnight, a suspension of tiny particles was observed, which was the aggregation of Compound I. When the suspension was heated, it turned clear. Interestingly, when the resulting solution was allowed to cool to room temperature, a suspension again resulted with retained morphologies and optical properties, thereby showing that these structures are thermodynamically stable. When a solution of Compound I in DMSO was drop cast on a pre-cleaned silicon substrate and subsequently dried in air at room temperature, nanofibers with high aspect ratio were observed by scanning electron microscopy as shown in FIG. 2(b). The nanofibers are interconnected and extend in one direction up to several micrometers and exhibit a net like structure.

To understand the effect of concentration on the self-assembly of the nanofibers of Compound I, solutions of different concentrations of Compound I in DMSO were prepared. When the concentration was lower than $10^{-4}$ M, only separated vesicles were obtained. When the concentration was increased, the vesicles started to aggregate and fuse together showing a stimulus free vesicle aggregation behavior to generate nanofibers which could be tuned by the concentration. At higher concentration, more number of Compound I molecules were involved in the self-assembly, and the intermolecular interactions such as π-π stacking and H-bonding interactions were strengthened accordingly. Thus, the free energy of the self-assembly is sufficient at high concentration, allowing molecules to generate extended π-π stacking arrays to form nanofibers. At low concentration, the stacked arrays of Compound I molecules are less compact, favoring the formation of loosely packed vesicles.

Filtration Efficiency Measurement

For all performance tests, PM particles were generated from incense smoke by burning. Burning incense emits smoke containing particulate matter, gas products, and other organic compounds. The gas products include CO, $CO_2$, $NO_2$, $SO_2$ and other volatile organic compounds such as benzene, toluene, xylenes, aldehydes, and polycyclic aromatic hydrocarbons, which are absorbed mostly on particulate matter. The smoke PM particles have a size of 2.5 μm and 10 μm. The inflow concentration was controlled by diluting the smoke PM by air to a hazardous pollution level equivalent to the PM 2.5 index >300.

Figure 5B:
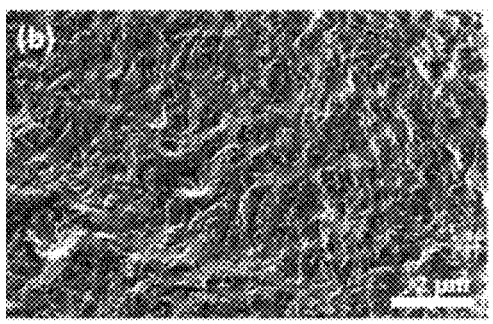

FIGS. 5(a) and 5(b) shows the SEM images of the nanofibers before and after exposure to PM particles. It can be seen that smoke PM formed a coating over the surface of the nanofibers.

Figure 6:
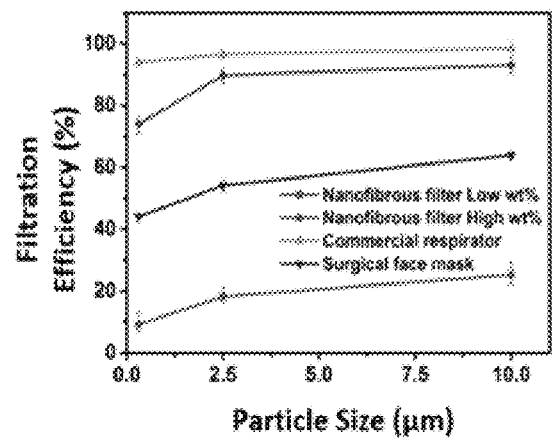
FIG. 6 shows a comparison of the filtration efficiency of different filters.

To test the filtration efficiency, nanofibrous filters with two different basis weights, 0.5 and 1.6 mg/cm$^2$ were prepared. PM particle number concentrations were detected with and without filters using a laser particle counter (LJ-0A5) and the filtration efficiency was calculated by comparing the number concentration before and after filtration. The capture efficiencies of nanofibrous filter with different basis weight is shown in FIG. 6. For the air filter with basis weight of 0.5 mg/cm$^2$, only 18% of PM 2.5 particles and 25% of PM 10 particles were captured. Low filtration efficiency of this filter was mainly because of the unoccupied holes of the mesh where no nanofibers hanging across the mesh were found and only corners of the mesh holes contained some nanofibers. When the air filter with basis weight of 1.6 mg/cm$^2$ was tested, 89.69% of the PM 2.5 particles and 93.08% of PM 10 particles could be filtered. At this concentration, the nanofibers were present across the mesh hardly left any unoccupied holes in the mesh.

To compare the filtration efficiency of the nanofibrous filters, a commercial respirator and surgical face mask that people use during increased pollution levels, were subjected to the same filtration test conditions as the nanofibrous filters. The commercial respirator mask was found to filter 96% of the PM 2.5 particles and 98% of the PM 10 particles whereas the surgical face mask was found to capture only 54% of the PM 2.5 particles and 63% of the PM 10 particles (see FIG. 6).

Figure 7:
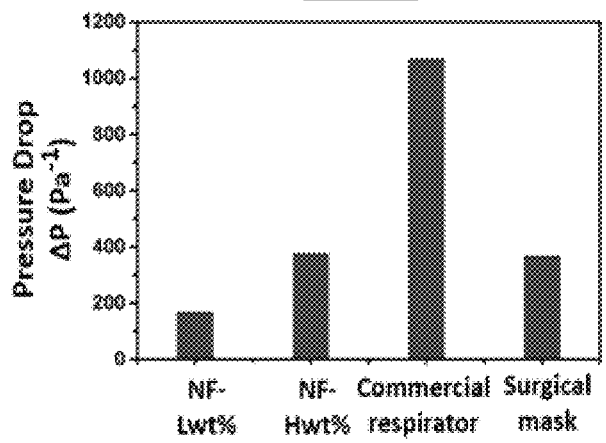
FIG. 7 shows a comparison of the pressure drop of different filters.

Another critical factor that determines the efficiency and potential of the air filters is the breathability test or the pressure drop, which is caused by the combined effects of the resistance of each fiber to the flow of air past it and should be low. Therefore, a highly efficient air filter should have a good balance between the PM particle removal efficiency and the pressure drop. FIG. 7 shows the pressure drop test for the nanofibrous filters (0.5 and 1.6 mg/cm$^2$), commercial respirator, and surgical face mask filter. A quantitative analysis of the air flow through the filters was carried out by measuring the pressure drop (ΔP) across the filters at a face velocity of 3 m/s. The pressure drop was measured by a differential pressure gauge (EM201B, UEi test instrument).

As expected the pressure drop for nanofibrous filter with basis weight of 0.5 mg/cm$^2$ was low at 167 Pa. For the nanofibrous filters with basis weight of 1.6 mg/cm$^2$, the pressure drop was increased to 374 Pa. However, for the commercial respirator filter which showed high PM particle removal efficiency, the pressure drop was found very high at 1067 Pa whereas the normal surgical face mask filter showed 366 Pa pressure drop. The high pressure drop in the case of the commercial respirator and surgical face mask is attributed to the multi-layered structure of these filters.

To determine the overall performance of the air filters, the quality factor (QF) was also calculated based on the experimental data of the filtration efficiencies and the pressure drops as:

$$QF = -\frac{\ln(1-\eta)}{\Delta P},$$

where η is the filtration efficiency, ΔP is the differential pressure drop, and OF is the quality factor.

Figure 8:
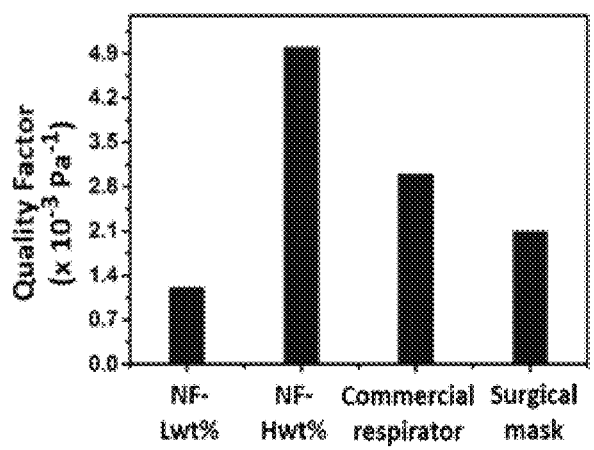
FIG. 8 shows a comparison of the quality factor of different filters.

An efficient air filter should have higher quality factor. FIG. 8 shows the comparison of the quality factor between the nanofibrous filters, commercial respirator and surgical face mask. The nanofibrous filter with low weight % has shown low QF value because of the very low removal efficiency. The QF of the higher weight % nanofibrous filter made a dramatic improvement showing significant increase because the filtration efficiency increase was more significant than the pressure drop increase. However, the quality factor value for the most commonly used commercial respirator during hazardous pollution levels was surprisingly found to be lower than the nanofibrous filter due to the increased pressure drop. The increased pressure drop is as a result of the commercial respirator's multi-layered design which blocks air flow. On the other hand, although the surgical mask has a low pressure drop, this could not compensate for its decreased filtration efficiency. The filtration efficiency is higher in the nanofibrous filter as the fibers are closely spaced.

Nanofibrous Filter Characteristics

Figure 9A:
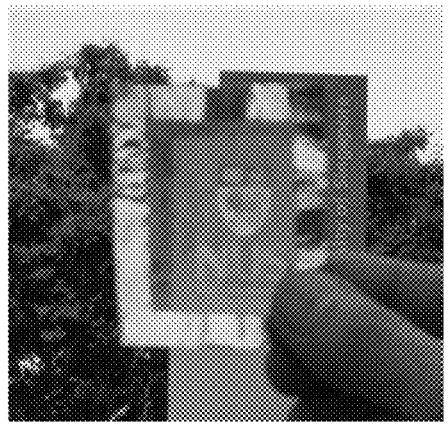
FIG. 9(a) shows a picture of the nanofibrous filter according to one embodiment of the present invention and FIGS. 9(b) and (c) show pictures of filters of prior art.
Figure 9B:
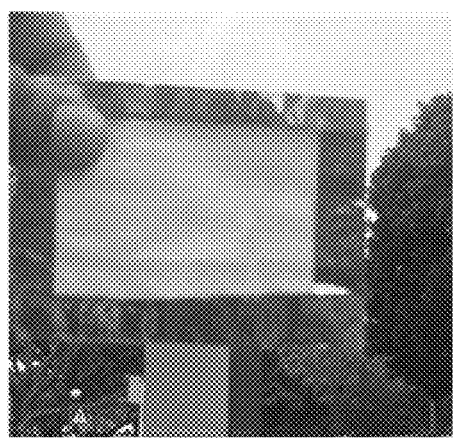
Figure 9C:
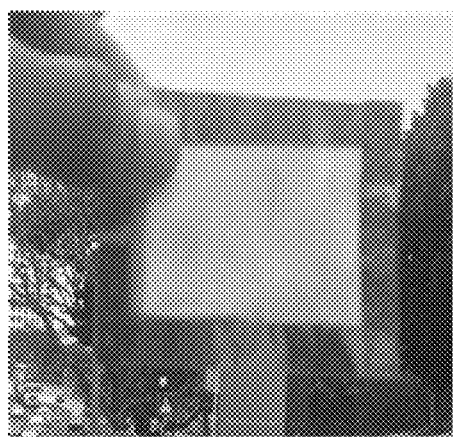

A digital image of the nanofibrous filter of the present invention is shown in FIG. 9(a). Comparing with FIGS. 9(b) and 9(c), it can be seen that the nanofibrous filter is transparent as compared to the commercial respirator (FIG. 9(b)) and the surgical mask based filter (FIG. 9(c)). In particular, commercial respirator and surgical face mask rely on the pore size of the filter material and consist of multiple layers for filtration compared to the nanofibrous filter of the present invention. Accordingly, the commercial respirator and surgical face mask depict no transmittance.

Figure 10:
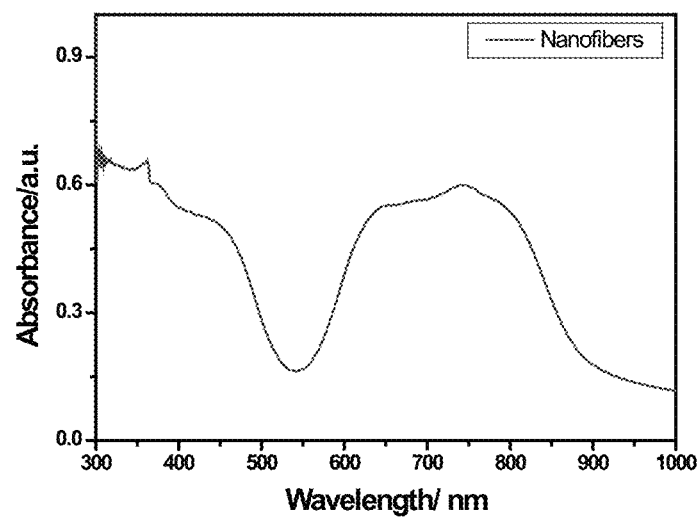
FIG. 10 shows an absorption spectrum of nanofibers of Compound I.

FIG. 10 shows the ultraviolet-visible (UV-vis) spectra obtained for the nanofibers formed from Compound I. The spectra was obtained using a Biochrom Libra S70 spectrophotometer at room temperature. The measurement was carried out using anhydrous DMSO at a sample concentration comprising $1\times10^{-4}$ M of the nanofibers. In particular, a light beam, filtered to a specific wavelength, was shone through the sample and onto a light meter. The data obtained determined the wavelength and amount of light absorbed by the sample. It can be seen from the obtained absorption spectrum that formation of H-type aggregates of compound I is present. In H-type aggregates, the molecules are preferably arranged in a face-to-face manner.

Example 2

Figure 11:
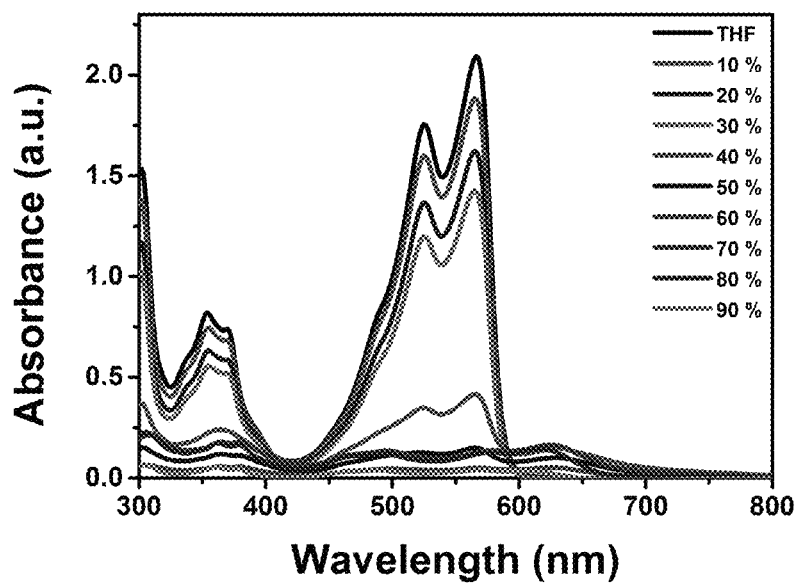
FIG. 11 shows a UV-visible absorption change in different THF-water fractions of Compound II.

Compound II was synthesised as per the synthesis scheme shown in FIG. 3. Once Compound II was synthesised, Compound II (1 mg) was dissolved in tetrahydrofuran (THF, 1 mL) to obtain a pink coloured solution. The solution formed had a concentration of $2\times10^{-5}$ M. The solution was then diluted with deionised water so that the final solution had a water fraction from 10% to 90%. The as prepared solutions were then analysed by an absorption spectrophotometer and the results obtained are shown in FIG. 11. The UV-visible absorption spectrum provides information about the intermolecular interactions of the molecules of Compound II. As can be seen from FIG. 11, there was a change in the absorption spectrum of compound II as the THF-water fraction reached 40%, specifically there was generation of a new band beyond the 600 nm region. This new band shows the formation of the nanofibers. In particular, the new band shows that several molecules of Compound II have assembled together. The assembly of the molecules with such absorption changes is the signature of J-type aggregates, where the molecules are arranged in a head to tail fashion. It can be seen that below 40% THF-water fraction, there was no new band formation beyond 600 nm, which means that the molecules are still separated from each other and the spectrum profile represents an individual molecule.

Figure 12:
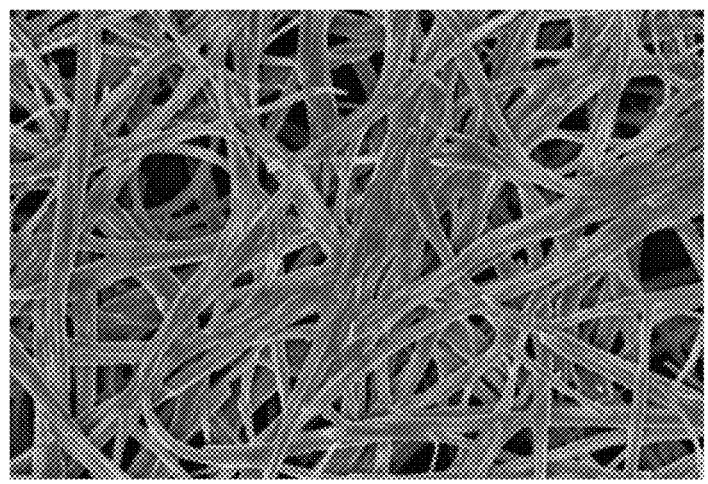
FIG. 12 shows a SEM image of the nanofibers of Compound II.

Accordingly, a 40% THF-water fraction solution was formed by using 0.6 mL of the prepared solution of Compound II dissolved in THF and diluting with 0.4 mL of deionized water. Upon addition of water, the colour of the solution changed to purple. The prepared solution was left to stand overnight. Thereafter, the solution turned into suspension, thereby suggesting that the molecules of Compound II had self-assembled into nanofibers. The suspension was drop cast on a pre-cleaned silicon substrate and subsequently dried in air at room temperature. From scanning electron microscopy, it could be seen that nanofibers with a high aspect ratio had been formed, as shown in FIG. 12.

While the invention has been described in detail, it will be apparent to one skilled in the art that various changes and modifications can be made and equivalents employed, without departing from the present invention. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

The invention claimed is:

1. A nanofibrous filter comprising a substrate and self-assembled nanofibers deposited on the substrate, the self-assembled nanofibers comprising π-conjugated molecules self-assembled by non-covalent interactions, wherein the π-conjugated molecules are phthalocyanine derivative molecules or diketopyrrolopyrrole derivative molecules.

2. The nanofibrous filter according to claim 1, wherein the non-covalent interactions comprise π-π stacking, intermolecular hydrogen bonding, or a combination thereof.

3. The nanofibrous filter according to claim 1, wherein the phthalocyanine derivative molecule is Compound I:

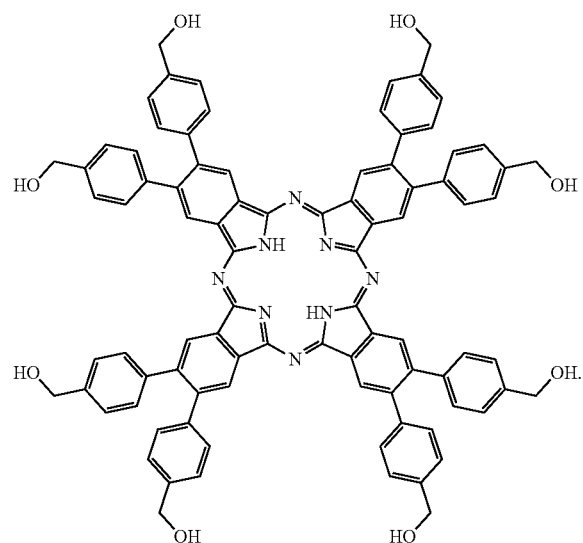 [SMILES: OCc1ccc(-c2cc3c(cc2-c2ccc(CO)cc2)-c2nc-3nc3[nH]c(nc4nc(nc5[nH]c(n2)c2cc(-c6ccc(CO)cc6)c(-c6ccc(CO)cc6)cc52)-c2cc(-c5ccc(CO)cc5)c(-c5ccc(CO)cc5)cc2-4)c2cc(-c4ccc(CO)cc4)c(-c4ccc(CO)cc4)cc32)cc1]

4. The nanofibrous filter according to claim 3, wherein the Compound I is formed by cyclotetramerization of 4,4''-bis(hydroxymethyl)-[1,1':2',1''-terphenyl]-4',5'-dicarbonitrile in 1-pentanol.

5. The nanofibrous filter according to claim 1, wherein the diketopyrrolopyrrole derivative molecule is Compound II:

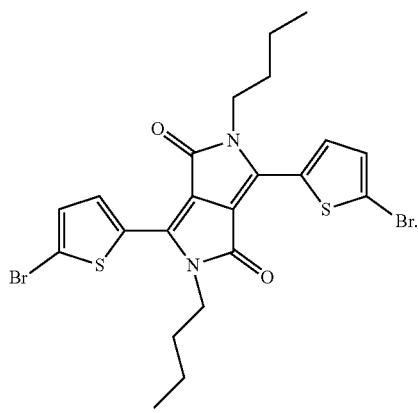 [SMILES: CCCCN1C(=O)C2=C(c3ccc(Br)s3)N(CCCC)C(=O)C2=C1c1ccc(Br)s1]

6. The nanofibrous filter according to claim 1, wherein the nanofibers have an average diameter of 100-300 nm.

7. The nanofibrous filter according to claim 1, wherein the nanofibrous filter has a filtration efficiency of ≥80% for PM 2.5 particles and ≥85% for PM 10 particles.

8. The nanofibrous filter according to claim 1, wherein the pressure drop across the filter is ≤400 Pa.

9. A method of preparing the nanofibrous filter of claim 1, wherein the method comprises:
obtaining π-conjugated molecules, wherein the π-conjugated molecules are phthalocyanine derivative molecules or diketopyrrolopyrrole derivative molecules;
dissolving the π-conjugated molecules in an organic solvent to form a solution comprising self-assembled nanofibers; and
depositing the solution on a surface of a substrate to form the nanofibrous filter.

10. The method according to claim 9, wherein the obtaining comprises synthesising the π-conjugated molecules.

11. The method according to claim 10, wherein the synthesising of the phthalocyanine derivative molecules comprises cyclotetramerization of 4,4''-bis(hydroxymethyl)-[1,1':2',1''-terphenyl]-4',5'-dicarbonitrile in 1-pentanol.

12. The method according to claim 9, wherein the organic solvent is selected from the group consisting of: dimethyl sulfoxide (DMSO), tetrahydrofuran (THF), dimethylformamide (DMF), dimethylacetamide (DMAc) or a combination thereof.

13. The method according to claim 12, wherein the organic solvent is DMSO when the π-conjugated molecule is phthalocyanine derivative molecule.

14. The method according to claim 12, wherein the organic solvent is THF when the π-conjugated molecule is diketopyrrolopyrrole derivative molecule.

15. The method according to claim 9, wherein the π-conjugated molecule is dissolved in the organic solvent at a concentration of $\geq 10^{-4}$ M when the π-conjugated molecule is phthalocyanine derivative molecule.

16. The method according to claim 9, wherein the π-conjugated molecule is dissolved in the organic solvent at a concentration of $\geq 10^{-5}$ M when the π-conjugated molecule is diketopyrrolopyrrole derivative molecule.

17. The method according to claim 9, wherein the depositing comprises drop-casting the solution on a surface of the substrate.

* * * * *

UNITED STATES PATENT AND TRADEMARK OFFICE
CERTIFICATE OF CORRECTION

| | |
|---|---|
| PATENT NO. | : 10,682,602 B2 |
| APPLICATION NO. | : 15/876000 |
| DATED | : June 16, 2020 |
| INVENTOR(S) | : Swee Ching Tan, Varun Kumar Singh and Sai Kishore Ravi |

Page 1 of 1

It is certified that error appears in the above-identified patent and that said Letters Patent is hereby corrected as shown below:

On the Title Page

Item (30), Foreign Application Priority Data, that document number reading "0201700455T" should read --10201700455T--.

Signed and Sealed this
Twenty-eighth Day of July, 2020

Andrei Iancu
*Director of the United States Patent and Trademark Office*